United States Patent
Salo et al.

(10) Patent No.: US 8,255,052 B2
(45) Date of Patent: Aug. 28, 2012

(54) TEMPERATURE BASED SYSTEMS AND METHODS FOR TACHYCARDIA DISCRIMINATION AND THERAPY

(75) Inventors: Rodney W. Salo, Fridley, MN (US); Allan Charles Shuros, St. Paul, MN (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 585 days.

(21) Appl. No.: 12/411,157

(22) Filed: Mar. 25, 2009

(65) Prior Publication Data

US 2009/0254137 A1  Oct. 8, 2009

Related U.S. Application Data

(60) Provisional application No. 61/041,688, filed on Apr. 2, 2008.

(51) Int. Cl.
*A61N 1/36* (2006.01)
(52) U.S. Cl. .................. 607/21; 607/6; 607/9
(58) Field of Classification Search .................. 607/21, 607/2, 6, 9
See application file for complete search history.

(56) References Cited

U.S. PATENT DOCUMENTS

| | | | |
|---|---|---|---|
| 5,005,574 A | 4/1991 | Fearnot et al. | |
| 5,063,927 A * | 11/1991 | Webb et al. | 607/18 |
| 5,156,148 A | 10/1992 | Cohen | |
| 5,179,945 A | 1/1993 | Van Hofwegen et al. | |
| 5,301,677 A | 4/1994 | Hsung | |
| 5,370,667 A | 12/1994 | Alt | |
| 5,782,879 A * | 7/1998 | Rosborough et al. | 607/6 |
| 5,814,087 A * | 9/1998 | Renirie | 607/21 |
| 5,897,576 A | 4/1999 | Olson et al. | |
| 6,658,286 B2 | 12/2003 | Seim | |
| 6,662,048 B2 | 12/2003 | Balczewski et al. | |
| 6,681,135 B1 * | 1/2004 | Davis et al. | 607/21 |
| 6,892,095 B2 | 5/2005 | Salo | |
| 7,127,291 B2 * | 10/2006 | Zhu et al. | 607/21 |
| 7,206,637 B2 | 4/2007 | Salo | |
| 7,577,478 B1 * | 8/2009 | Kroll et al. | 607/6 |
| 7,616,991 B2 * | 11/2009 | Mann et al. | 607/9 |
| 8,095,205 B2 * | 1/2012 | Bhunia | 600/509 |
| 2005/0096706 A1 | 5/2005 | Salo | |

OTHER PUBLICATIONS

PCT International Search Report and Written Opinion from International Application No. PCT/US2009/038743, corresponding to U.S. Appl. No. 12/411,157, mailed Jul. 7, 2009, pp. 1-17.
Yoon, Yeo-Sun et al., "Automated Analysis of Intracardiac Blood Pressure Waveforms for Implantable Defibrillators", *Computers in Cardiology* 1998, vol. 25, pp. 269-272.

(Continued)

*Primary Examiner* — George Evanisko
*Assistant Examiner* — Christopher A Flory
(74) *Attorney, Agent, or Firm* — Pauly, DeVries Smith & Deffner, LLC

(57) ABSTRACT

Embodiments of the invention are related to an implantable medical system, amongst other things. In an embodiment, the invention includes a processor, an electrical sensor, and a temperature sensor. The processor is configured to monitor myocardial electrical activity with input from the electrical sensor; identify myocardial electrical activity indicative of an arrhythmia, measure temperature of blood in the coronary venous system with input from the temperature sensor; determine if the arrhythmia is hemodynamically stable or hemodynamically unstable based on the temperature of blood in the coronary venous system, and initiate high-voltage shock therapy if the arrhythmia is hemodynamically unstable. Other embodiments are also included herein.

14 Claims, 9 Drawing Sheets

OTHER PUBLICATIONS

Hiles et al., "Detection of Ventricular Tachycardia and Fibrillation Using Coronary Sinus Blood", *Pacing and Clinical Electrophysiology*, 16(12):2266-2278 (1993).

Wolfe et al., "Update on implantable cardioverter-defibrillators", *Postgraduate Medicine*, vol. 103, No. 1 (Jan. 1998).

* cited by examiner

TEMPERATURE BASED SYSTEMS AND METHODS FOR TACHYCARDIA DISCRIMINATION AND THERAPY

This application claims priority to provisional U.S. patent application 61/041,688, filed Apr. 2, 2008, the contents of which are herein incorporated by reference.

TECHNICAL FIELD

This disclosure relates generally to medical devices and, more particularly, to systems and methods for tachycardia discrimination, amongst other things.

BACKGROUND OF THE INVENTION

Tachycardia is a heart condition defined in an adult as a heart rate faster than 100 beats/minute. Tachycardia can broadly be classified as either sinus tachycardia, supraventricular tachycardia, or ventricular tachycardia. Sinus tachycardia is generally caused by exercise or emotional stress and is usually non-pathological. Supraventricular tachycardia is defined as a tachycardia that originates above the bifurcation of the bundle of His. Supraventricular tachycardia generally does not result in significant decreases in cardiac output. Ventricular tachycardia is defined as a tachycardia that originates below the bifurcation of the bundle of His. Ventricular tachycardia can result in profound decreases in cardiac output.

Discrimination between the various types of tachycardia is important to the effective management of patients with heart conditions. This is because some instances of tachycardia can be quite normal and would not warrant therapeutic intervention, while others can have serious consequences including chest pain, syncope, and death. One way of assessing the seriousness of a tachycardia is by evaluating its effect on cardiac output. Tachycardia that leads to insufficient cardiac output can be referred to as hemodynamically unstable tachycardia. In contrast, tachycardia where cardiac output remains sufficient to sustain life can be referred to as hemodynamically stable tachycardia.

Implantable medical devices are used to treat patients with various conditions of the heart including tachycardia. In some cases, an implantable device is used to deliver a high-energy shock to a patient's heart to terminate a tachycardia. High-energy shocks are generally successful at terminating tachycardia. However, such shocks cause extreme discomfort for patients. In addition, such shocks also use a substantial amount of energy and thus shorten the battery life of the device.

Many types of cardiac rhythm management (CRM) devices are capable of detecting abnormalities of heart rhythm through the analysis of myocardial electrical activity. However, it remains difficult to discriminate between different types of tachycardia using only myocardial electrical activity.

For at least these reasons, a need remains for systems and methods of discriminating between different types of tachycardia.

SUMMARY OF THE INVENTION

Embodiments of the invention are related systems and methods of tachycardia discrimination that utilize temperature measurement as part of the analysis. In an embodiment, the invention includes a method of providing treatment to a patient including monitoring myocardial electrical activity with an electrical sensor, identifying myocardial electrical activity indicative of an arrhythmia, measuring temperature of blood in the coronary venous system with a temperature sensor, and determining if the arrhythmia is hemodynamically stable or hemodynamically unstable based on the temperature or short-term change in temperature of blood in the coronary venous system.

In an embodiment, the invention includes an implantable medical system including a processor, an electrical sensor, and a temperature sensor. The processor can be configured to monitor myocardial electrical activity with input from the electrical sensor, identify myocardial electrical activity indicative of an arrhythmia, measure temperature of blood in the coronary venous system with input from the temperature sensor, and determine if the arrhythmia is hemodynamically stable or hemodynamically unstable based on the temperature or short-term change in temperature of blood in the coronary venous system.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
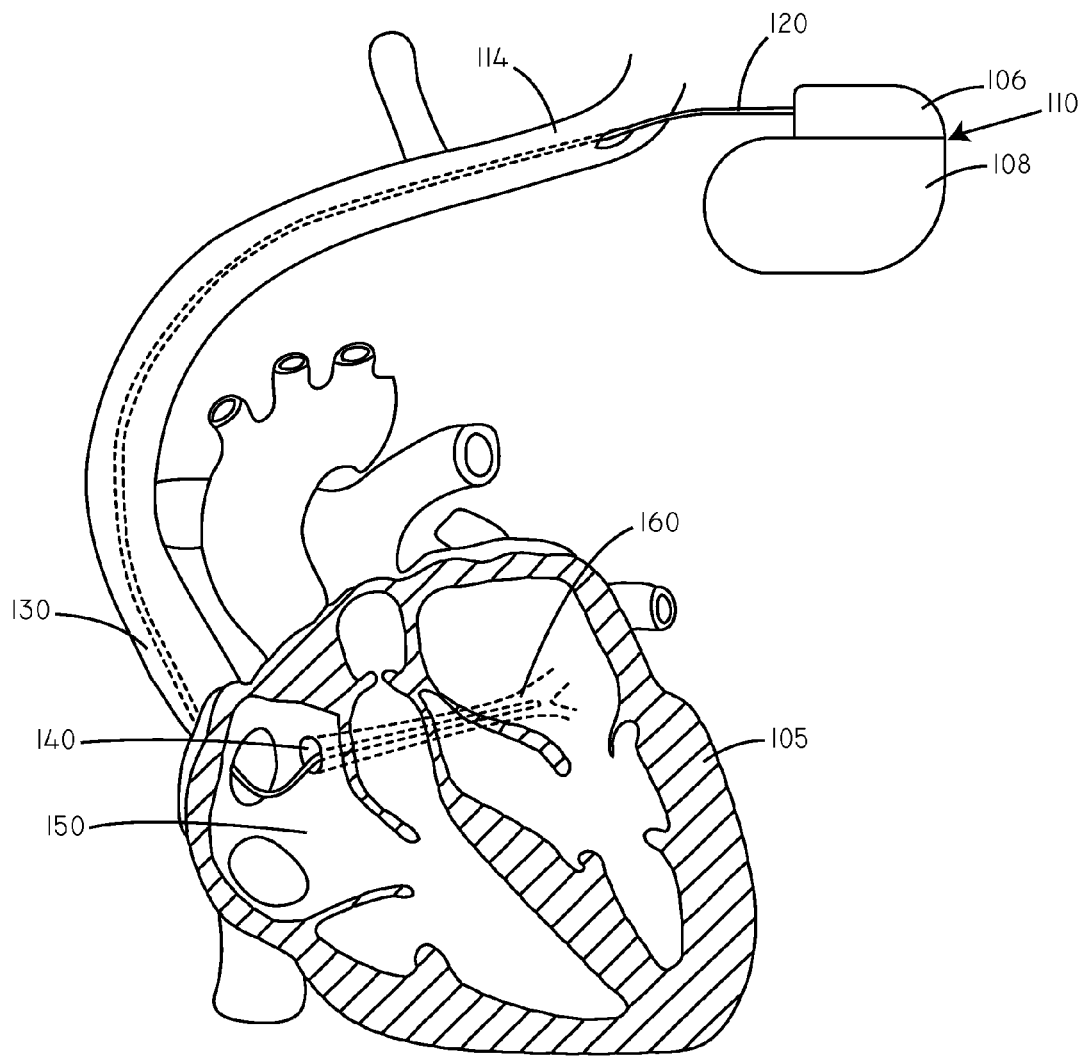
FIG. 1 is a schematic of an example implementation consistent with at least one embodiment of the technology disclosed herein.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Various types of tachycardia are frequently treated with high-voltage shock therapy in order to restore normal heart rhythm. Such therapy can be administered with an external defibrillator or an implantable cardiac rhythm management (CRM) device. However, because of patient discomfort, there is a desire amongst many clinicians to only deliver high-voltage shock therapy when the situation requires it. In the case of an external defibrillator, a clinician or emergency responder can make the decision as to whether or not a high-voltage shock is warranted based on three inputs: the underlying cardiac rhythm, the presence of a pulse, and a subjective assessment of the consciousness of the patient. However, in the case of an implantable CRM device, the device must be programmed in order to automatically determine when to deliver shocks. Most CRM devices identify arrhythmias through the analysis of myocardial electrical activity. However, it remains difficult to program a device to accurately discriminate between arrhythmias warranting high-voltage shock therapy (such as rhythms with low hemodynamic output) and arrhythmias treatable via other techniques such as anti-tachycardia pacing (ATP).

Cardiac parameters that can be impacted by tachycardia, including cardiac output and cardiac workload, can result in measurable changes in the temperature of blood. Blood perfusing the myocardium carries away heat generated by the heart during the contractile process. Thus, the temperature of blood in the coronary sinus is higher than that in the left ventricle and this temperature difference is related both to the workload of the heart and to the rate at which blood is flowing through the heart. The latter is largely determined by the cardiac output. If the temperature of blood in the left ventricle or aorta is assumed to be relatively constant, short-term changes in coronary sinus blood temperature are indicative of changes in the workload of the heart and/or changes in cardiac output.

In sinus tachycardia, an increase in temperature of coronary venous blood is expected due to increased workload of the myocardium, however the increase is not dramatic since cardiac output also increases providing an additional volume of blood flowing through the coronary venous system. In supraventricular tachycardia, no substantial change in temperature of coronary venous blood is expected because neither left ventricular output nor left ventricular workload are expected to change significantly. However, in ventricular tachycardia, a dramatic increase in the temperature of coronary venous blood is expected since myocardial work increases sharply while cardiac output decreases, reducing the volume of blood flowing through the coronary venous system. The relationships between these types of tachycardia and coronary venous (CV) blood temperature are shown below in Table 1.

TABLE 1

| | Type of Tachycardia | | |
| --- | --- | --- | --- |
| | Sinus | Supraventricular | Ventricular |
| Effect on CV Blood Temperature | Moderate Increase | No Increase | Sharp Increase |

In the context of an unstable tachyarrhythmia, the heart muscle typically has a high workload and therefore generates a significant amount of heat, but does not pump out sufficient amounts of blood. As such, the large amount of generated heat is transferred to a reduced volume of blood flowing through the coronary venous system, resulting in a significant and rapid increase in coronary venous temperature. Because of this effect, stability of an arrhythmia can be assessed by evaluating the change in temperature of blood in the coronary venous system. The relationship between these stable and unstable types of tachycardia and coronary venous (CV) blood temperature are shown below in Table 2.

TABLE 2

| | Type of Tachycardia | |
| --- | --- | --- |
| | Hemodynamically Stable | Hemodynamically Unstable |
| Effect on CV Blood Temperature | No Increase or Moderate Increase | Sharp Increase |

As such, embodiments of the invention can include systems and methods of determining whether an arrhythmia is hemodynamically stable or unstable based on change in coronary venous temperature. Embodiments of the invention can also include systems and methods of discriminating between sinus tachycardia, supraventricular tachycardia, and ventricular tachycardia based on change in coronary venous temperature. Embodiments of the invention can also include systems and methods of delivering therapy to a patient based in part on coronary venous temperature. Various aspects of exemplary embodiments will now be described in greater detail.

Referring now to FIG. 1, a system according to an embodiment of the present invention is shown deployed within a heart 105. The system includes a lead 120 that is designed for implantation into the coronary venous system. The lead 120 can be an electrical stimulation lead and/or a monitoring lead. The lead 120 has an elongated shape with dimensions suitable for transvenous implantation. A pulse generator 110 is coupled to the lead 120. The pulse generator 110 can include a header 106 and a pulse generator housing 108. The pulse generator 110 can receive and process electrical signals from the lead 120, such as signals related to myocardial electrical activity. In some embodiments the pulse generator 110 can also deliver electrical stimulation pulses and/or shocks through the lead 120 to the heart 105.

The pulse generator 110 typically includes a power supply and programmable circuitry. In some embodiments the pulse generator 110 can also include an electrical stimulation delivery system. The electrical stimulation delivery system may include, for example, capacitors and signal conditioning circuitry known in the art. The pulse generator 110 can also include components such as analog to digital (A-D) converters, D-A converters, amplifiers, filters, and the like. Further components of an exemplary pulse generator are described with respect to FIG. 3 below.

It will be appreciated that in some embodiments the system may also be adapted for monitoring purposes only, in which case the pulse generator 110 may not include an electrical stimulation delivery system. Further, although the pulse generator 110 is typically implantable, it can be appreciated that a pulse generator 110 can be externally located, in whole or in part, in some applications, such as a temporary installation or in clinical testing.

The lead 120 can be implanted into the coronary venous system using various techniques. In one such technique, as illustrated in FIG. 1, the lead 120 is guided through the left subclavian vein 114 and into the right atrium 150 of the heart via the superior vena cava 130. From the right atrium 150, the lead 120 is guided into the coronary sinus ostium 140. The lead 120, in some embodiments, can be guided through the coronary venous system 160 and the distal end of the lead 120 can be lodged therein.

Figure 2:
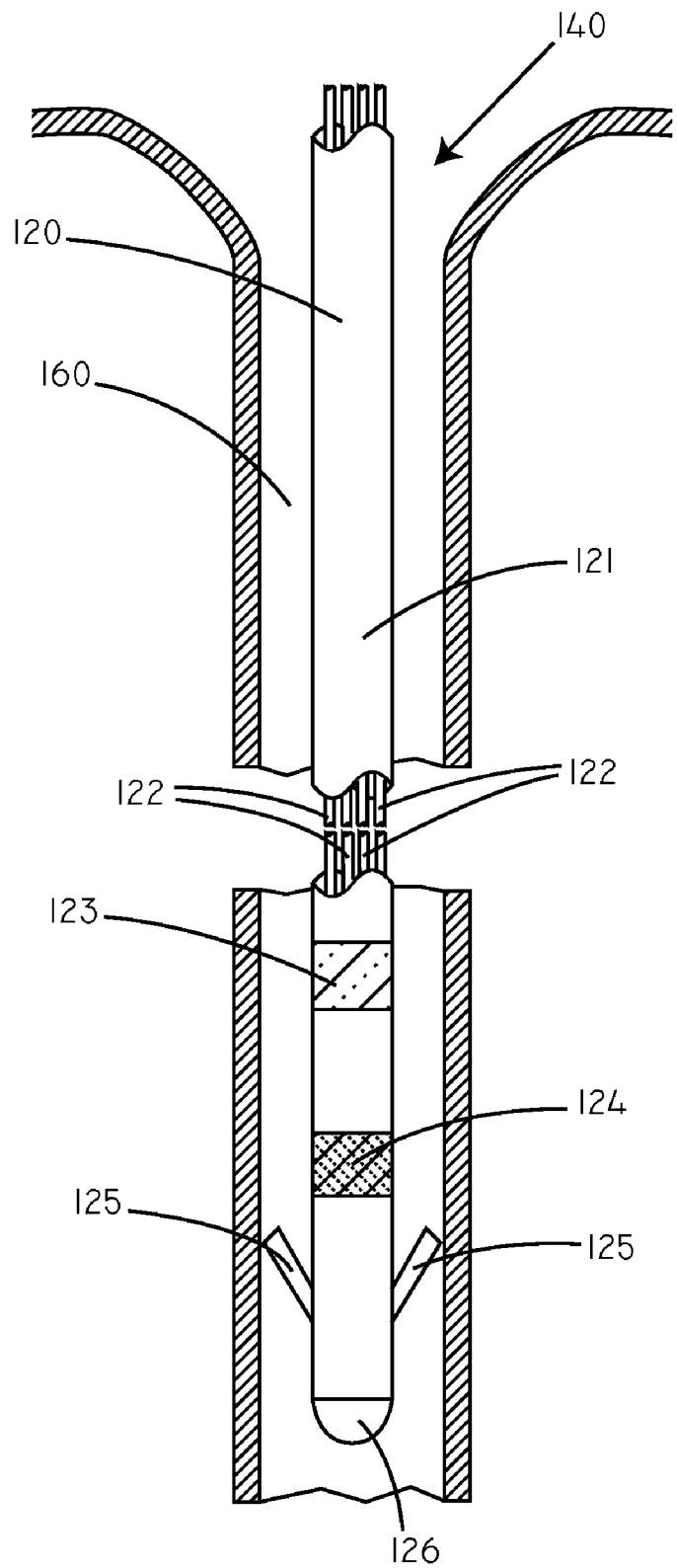
FIG. 2 is an embodiment of the technology disclosed herein consistent with at least the example implementation depicted in FIG. 1.

FIG. 2 is a schematic view of the distal end of the lead 120 depicted in FIG. 1 disposed within the coronary venous system 160. The lead 120 includes a sheath 121 and passes through the ostium 140 of the coronary venous system. Disposed within the sheath 121 are conductors 122 serving to provide electrical communication through the lead 120. Though four conductors are shown in FIG. 2, it will be appreciated that in various embodiments different numbers of conductors can be included. Disposed along the sheath 121 are electrodes 123, 126 and a temperature sensor 124. The electrode 126 adjacent to the tip of the lead 120 can be referred to as the tip electrode. The other electrode 123 can be referred to as the ring electrode. Each of the electrodes is in electrical communication with at least one of the conductors. In various embodiments, the temperature sensor 124 is in electrical communication with at least two of the conductors. The lead 120 can include fixation elements 125 to anchor the lead 120 within the coronary venous system 160.

The sheath 121 is generally constructed of a biocompatible material, and more particularly can be constructed of any material known in the art to provide relative isolation of the conductors 122 from bodily fluids. The sheath 121, in some embodiments, can comprise one or more polymers.

The ring electrode 123 and the tip electrode 126 can serve to transmit electrical signals between the lead and the tissue of the heart. However, in some embodiments, the lead 120 may only include a single electrode and the housing of the pulse generator itself can serve as a second electrode. It will be appreciated that the ring electrode 123 and the tip electrode 126 generally can be formed of a biocompatible conductor, and can include any biocompatible conductor known in the art for use as an implantable electrode. The ring electrode 123 and the tip electrode 126 can be, for example, a stainless steel alloy, platinum or platinum alloy, an iridium alloy, or the like. The ring electrode 123 and the tip 126 electrode need not be the same type of material. In some embodiments, the lead 120 may include additional electrodes, such as a shocking coil.

The temperature sensor 124 can be configured to respond to the temperature of its environment so that the temperature can be measured. In some embodiments the temperature sensor 124 is a thermistor, and changes in resistance changes are used by a processor within the pulse generator to calculate the temperature. The temperature sensor 124 can be constructed of a substantially biocompatible material. It will be appreciated that additional types of temperature sensors 124 can be included herein such as thermocouples, temperature sensitive diodes, fiber-optic temperature sensors and the like. In some embodiments the temperature sensor has a resolution of less than or equal to approximately 0.01 degrees Celsius.

In some embodiments, temperature can be measured in a variety of additional locations, such as in the left atrium or ventricle, the pulmonary artery or in the venous system outside the heart. Such additional temperature measurements can provide a control for fluctuations in core body temperature.

In some embodiments, the system can use additional data inputs when discriminating between tachycardia types. By way of example, in some embodiments the system can include physical activity sensor(s). Exemplary physical activity sensors can include a minute ventilation (MV) sensor and/or an accelerometer. Signals from physical activity sensors can be processed in order identify when exercise or other physical activity is taking place. As such, signals from such sensors can be used to distinguish or differentiate sinus tachycardia from other types of tachycardia.

Embodiments of the invention can specifically include implantable systems including an implantable medical device, such as a CRM device, along with one or more electrical stimulation leads, and one or more temperature sensors. Implantable medical devices can specifically include pacemakers, implantable cardioverter-defibrillators (ICDs), cardiac resynchronization therapy (CRT) devices, and the like.

Figure 3:
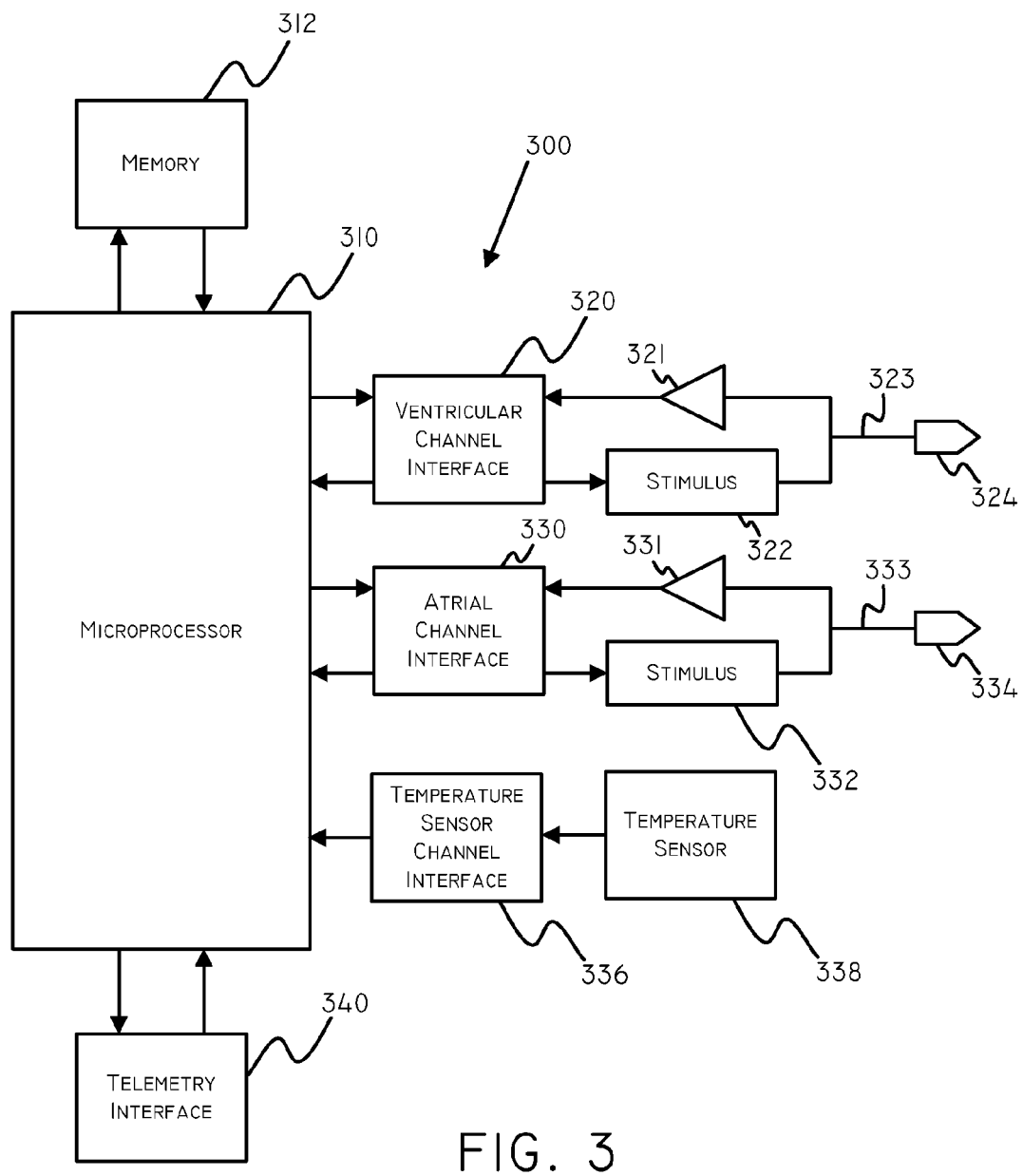
FIG. 3 is a diagram of various components of devices in accordance with various embodiments of the invention.

Elements of some embodiments of an implantable medical device are shown in FIG. 3. However, it will be appreciated that some embodiments can include additional elements beyond those shown in FIG. 3. For example, many embodiments would also include a power supply such as a battery, though not shown in FIG. 3. In addition, some embodiments may lack certain elements shown in FIG. 3.

The medical device 300 can monitor myocardial electrical activity and sense cardiac events, such as arrhythmias, through one or more sensing channels and can output electrical stimulation pulses to the heart via one or more stimulation channels. A microprocessor 310 communicates with a memory 312 via a bidirectional data bus. The memory 312 typically comprises ROM and/or RAM. A telemetry interface 340 is also provided for communicating with an external programmer.

In some embodiments, the implantable medical device has atrial sensing and stimulation channels comprising at least a first electrode 334, lead 333, sensing amplifier 331, output circuit 332, and an atrial channel interface 330 which communicates bidirectionally with a port of microprocessor 310. In some embodiments, the device also has ventricular sensing and stimulation channels comprising at least a second electrode 324, lead 323, sensing amplifier 321, output circuit 322, and ventricular channel interface 320. For each channel, the same lead and electrode can be used for both sensing and stimulation. The channel interfaces 320 and 330 can include analog-to-digital converters for digitizing sensing signal inputs from the sensing amplifiers and registers which can be written to by the control circuitry in order to change the stimulation pulse amplitude, and adjust the gain and threshold values for the sensing amplifiers.

In some embodiments, the implantable medical device can also include a shocking output circuit (not shown in FIG. 3). The shocking output circuit can include one or more capacitors that can be charged and then rapidly discharged in order to create a shock that can then be delivered to tissue via electrodes, such as a shocking coil.

The implantable medical device can also include at least one temperature sensor 338, such as a thermistor, a thermocouple, a temperature sensitive diode, a fiber-optic temperature sensor or the like, and a temperature sensor channel interface 336 that can include analog-to-digital converters for digitizing signal inputs from the temperature sensor 383 and submitting the signals for further processing by the microprocessor 310. Processing of a signal can include various operations such as converting the signal into information regarding temperature, or temperature change, storing signal information signal, and the like. In some embodiments there are two temperature sensors. In some embodiments, there are more than two temperature sensors.

In some embodiments, the implantable medical device can also include other types of sensors beyond electrical activity sensors and temperature sensors. For example, in some embodiments the implantable medical device can also include chemical sensors, physical activity sensors, and the like. As such, the system can include a physical activity sensor channel interface and a physical activity sensor. Exemplary physical activity sensors can include minute ventilation (MV) sensors and accelerometers. It will be appreciated that minute ventilation sensors can operate in various ways such as by measuring transthoracic impedance. In some embodiments, the system can perform the step of assessing physical activity with a physical activity sensor to distinguish between sinus tachycardia and other types of tachycardia such as supraventricular tachycardia and ventricular tachycardia.

The processor 310 can be configured to use the signals from the electrodes in order to identify myocardial electrical activity indicative of an arrhythmia. The myocardial electrical activity can comprise a time-varying electrical potential. In some embodiments, the processor can calculate an R-R interval time. In some embodiments, an R-R interval time of less than about 600 milliseconds can be indicative of a tachycardia. Techniques for identifying arrhythmias from myocardial electrical activity are described in U.S. Pat. Nos. 6,658,286 and 5,301,677, for example, the content of which is herein incorporated by reference in its entirety. Other techniques for identifying tachycardia, and specifically non-sinus tachycardias, that can be used with embodiments herein can include evaluating how quickly the heart rate increases and evaluating changes in the morphology of the electrical activity of the heart. In some embodiments, when an arrhythmia is identified a capacitor is charged so that the device can be made ready to deliver a shock.

In some embodiments, when a tachycardia is identified, the system can be configured to use temperature data in order to classify the tachycardia or discriminate between different types of tachycardia. In some embodiments the temperature sensor is turned on only after myocardial electrical activity indicative of an arrhythmia is identified by the system. In other embodiments, the temperature sensor is turned on continuously. In some embodiments, the system can start charging a capacitor at the same time that temperature measurements are being assessed.

The system can be configured to use one or more temperature based parameters when classifying the tachycardia. Exemplary temperature based parameters can include the absolute temperature, the change in temperature over the temperature prior to the onset of episode, the change in temperature over a baseline value for temperature where the baseline could represent an average over a period of time, the average rate of temperature change during onset of an episode (dT/dt AVG), the maximum rate of temperature change observed during a specific period of time (dT/dt MAX), or the like.

After temperature parameters are assessed, the system can then use this temperature information to classify and/or confirm the tachycardia. For example, the system can use the temperature information to classify the tachycardia is either a sinus tachycardia, a supraventricular tachycardia, or a ventricular tachycardia. This can be done in various ways. For example, the current value of the parameter can be compared against some baseline value or set of baseline values. As another example, the current parameter value can be compared against a threshold value or set of threshold values.

Figure 4:
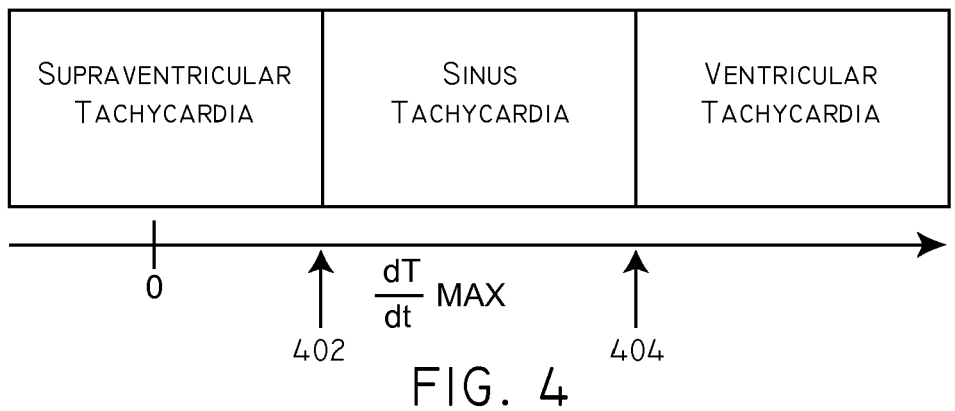
FIG. 4 is a diagram illustrating one example of how tachycardia can be classified using temperature parameter data.
Figure 5:
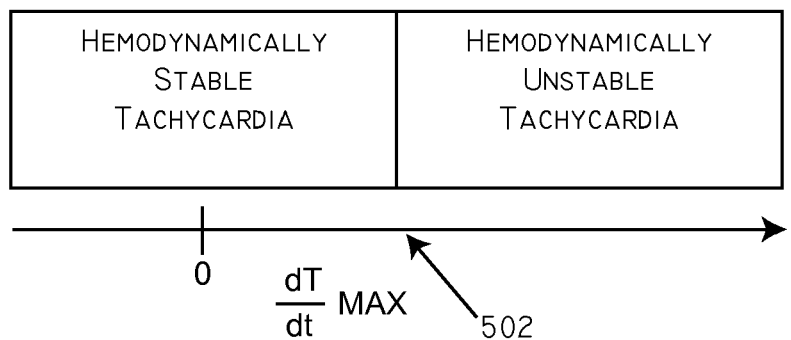
FIG. 5 is a diagram illustrating another example of how tachycardia can be classified using temperature parameter data.
Figure 6:
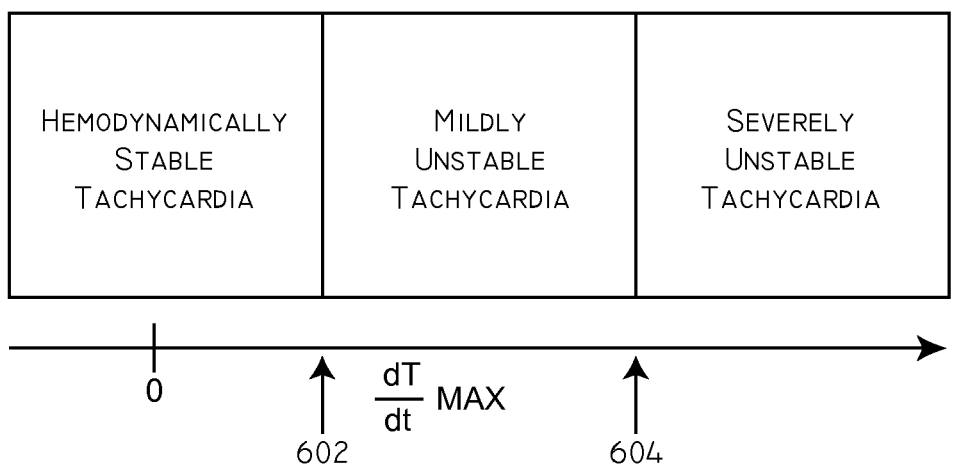
FIG. 6 is a diagram illustrating another example of how tachycardia can be classified using temperature parameter data.

For example, referring now to FIG. 4, a diagram is shown illustrating how the maximum rate of temperature change during a period of time or during an episode (dT/dt MAX) can be used to classify a tachycardia as either supraventricular tachycardia, sinus tachycardia, or ventricular tachycardia. For example, if the observed dT/dt MAX is less than a first threshold amount 402, the episode is classified as being supraventricular tachycardia. If the observed dT/dt MAX falls in between the first threshold amount 402 and a second threshold amount 404, the episode is classified as being sinus tachycardia. If the observed dT/dt MAX is greater than a second threshold amount 404, the episode is classified as being ventricular tachycardia. Though two threshold amounts are depicted in FIG. 4, it will be appreciated that greater or lesser numbers of threshold amounts can be used in various embodiments. Referring now to FIG. 5, a diagram is shown illustrating how the maximum rate of temperature change during a period of time or during an episode (dT/dt MAX) can be used to classify a tachycardia as either hemodynamically stable or hemodynamically unstable. In this embodiment, hemodynamically stable tachycardia can be distinguished from hemodynamically unstable tachycardia using a single threshold amount 502. Finally, referring to FIG. 6, a diagram is shown illustrating how the maximum rate of temperature change during a period of time or during an episode (dT/dt MAX) can be used to classify a tachycardia as either hemodynamically stable, mildly unstable, or severely unstable using a first threshold amount 602 and a second threshold amount 604.

In at least one embodiment, the temperature at the time an arrhythmia is identified is compared to the average temperature over a particular time period to classify the particular arrhythmia. In some embodiments, the time period for calculating the average temperature can span from about two seconds to about five minutes. Though in other embodiments, the time period can be greater than five minutes or less than two seconds.

It will be appreciated that differences may exist between patients with regard to how the temperature of their coronary venous blood may change in response to conditions such as exercise. As such, in some embodiments, the system can be calibrated after implantation within a patient. For example, a patient with an implanted system as described herein can be subjected to a stress test and the effect on coronary venous temperature can be recorded. Then the system baseline can be set according to the observed temperature change during the stress test. In some embodiments, the maximal rate of coronary venous blood temperature change observed during the stress test (dT/dt MAX), or some multiple thereof, can serve as the threshold value for distinguishing between hemodynamically stable and hemodynamically unstable tachycardia. Alternatively, the maximal rate of coronary venous blood temperature change observed, or some multiple thereof, can serve as the threshold value for distinguishing between sinus tachycardia and ventricular tachycardia.

In some embodiments, the values of dT/dt or dT/dt MAX that are used to distinguish between the different types of tachycardia can start off as a default value and can then be changed through techniques such as manual changes made using a PRM (programmer/recorder/monitor) device, automatic changes through an algorithm, or the like.

In some embodiments, if a hemodynamically unstable or severely unstable arrhythmia is detected, the processor can initiate, and the pulse generator 110 can deliver, high voltage shock therapy to the heart through the lead 120 to restore and maintain normal heart rhythm. The high-voltage shock can be delivered by discharging a charged capacitor. The high voltage shock, for example, can comprise a pulse of current at greater than about 200 volts.

In some embodiments, if a hemodynamically stable arrhythmia is detected, anti-tachycardia pacing therapy is delivered. Some aspects of anti-tachycardia pacing therapy are described in U.S. Pat. No. 6,885,890, the content of which is herein incorporated by reference in its entirety. In other embodiments, anti-tachycardia pacing therapy is delivered if the arrhythmia is categorized as an unstable arrhythmia. In such an embodiment, a high voltage shock can be delivered by discharging the capacitor if anti-tachycardia pacing does not resolve an identified arrhythmia.

Figure 7:
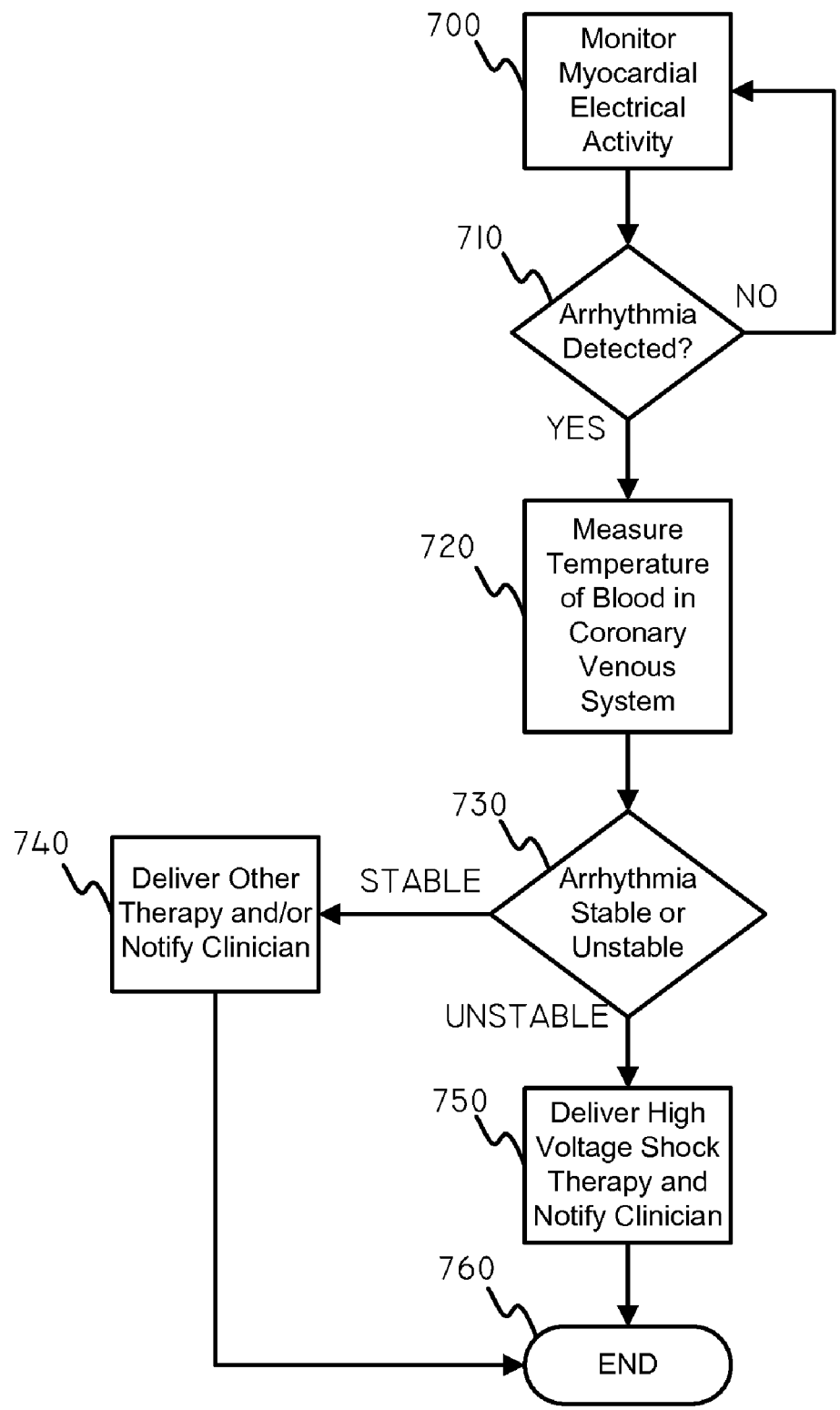
FIG. 7 is a flow diagram of an embodiment consistent with the technology disclosed herein.

FIG. 7 is a flow diagram consistent with at least one embodiment of the technology disclosed herein. Myocardial electrical activity is monitored 700, and it is determined whether an arrhythmia is detected 710. If an arrhythmia is not detected, the system continues to monitor myocardial activity 700. If an arrhythmia is detected, the temperature of the blood in the coronary venous system is measured 720, and the arrhythmia is determined to be stable or unstable 730. If the arrhythmia is stable, a clinician is notified and/or other therapy is delivered 740, and the process ends 760. However, if the arrhythmia is unstable, high voltage shock therapy is delivered 750 and a clinician is notified, after which the process ends 760.

In some embodiments, blood temperature can also be monitored after administration of therapy in order to verify termination of the arrhythmia.

As mentioned in the discussion of FIG. 3, above, the arrhythmia can be determined to be stable or unstable 730 by the processor based on temperature. If the arrhythmia is stable, when the clinician is notified and/or other therapy is delivered 740 it can be through a means that is known in the art. The clinician can be notified through a telemetry interface, for example, that can provide visual, audio, or alternate means of communication of the stable arrhythmia. Additionally, other therapy can be delivered 740 consistent with any means known in the art to treat similar arrhythmias such as drug treatments or physical maneuvers. If the arrhythmia is unstable, high voltage shock therapy can be delivered 750 automatically from the system itself, or through any other means known in the art.

Figure 8:
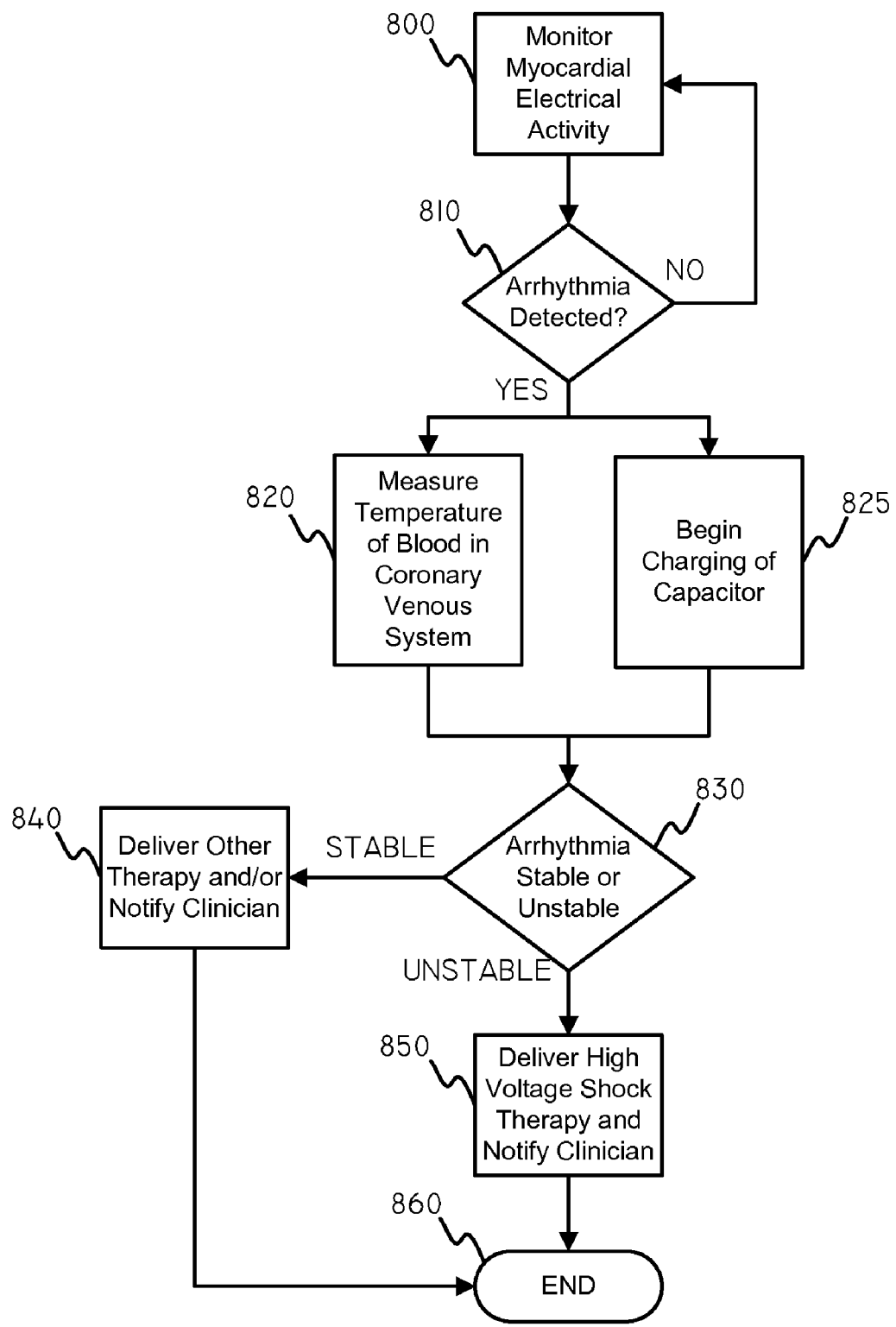
FIG. 8 is a flow diagram of an alternative embodiment consistent with the technology disclosed herein.

FIG. 8 is a flow diagram of an alternative embodiment consistent with the technology disclosed herein. The system monitors 800 myocardial electrical activity in order to try to identify arrhythmias. In this embodiment if an arrhythmia is detected 810 the temperature of blood in the coronary venous system is measured 820 in conjunction with the capacitor being charged 825. In this way the system 800 prepares itself in the event that high voltage shock therapy ultimately needs to be delivered. Based on the temperature data, the system can determine whether the arrhythmia is stable or unstable 830. If the arrhythmia is stable, a clinician is notified and/or other therapy is delivered 840, and the process ends 860. However, if the arrhythmia is unstable, high voltage shock therapy is delivered 850 and a clinician is notified, after which the process ends 860.

Figure 9:
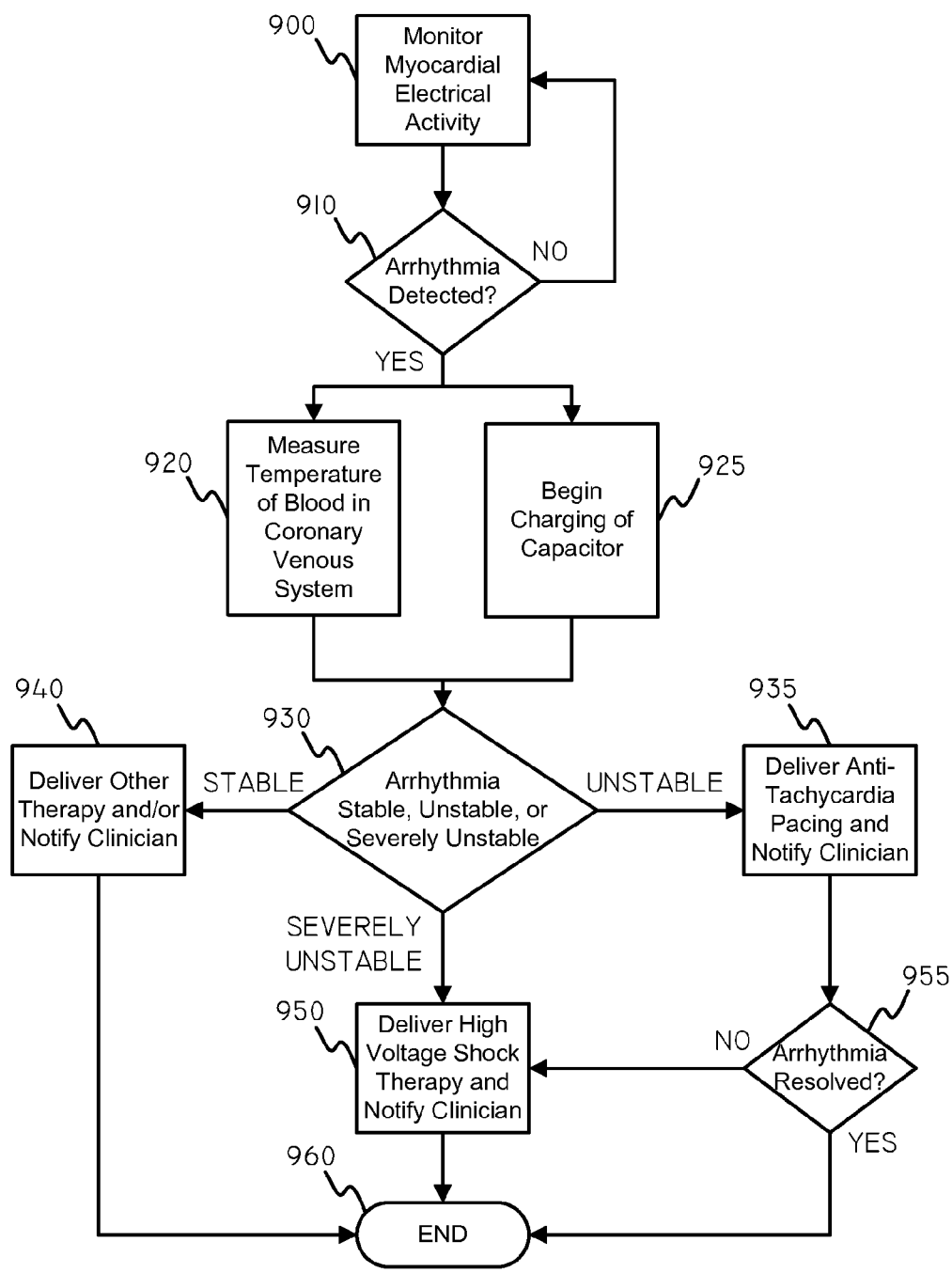
FIG. 9 is a flow diagram consistent with at least one embodiment of the technology disclosed herein.

FIG. 9 is a flow diagram of an alternative embodiment consistent with the technology disclosed herein. The system monitors 900 myocardial electrical activity in order to try to identify arrhythmias. Similar to the previous embodiment, if an arrhythmia is detected 910 the temperature of blood in the coronary venous system is measured 920 in conjunction with the capacitor being charged 925. The system then classifies the arrhythmia as either stable, unstable, or severely unstable 930. If the arrhythmia is stable, a clinician is notified and/or other therapy is delivered 940, and the process ends 960. If the arrhythmia is severely unstable, then high voltage shock therapy is delivered 950 and a clinician is notified, after which the process ends 960. However, if the arrhythmia is unstable but less than severely unstable, then the system can deliver anti-tachycardia pacing (ATP) 935. The system can then evaluate whether ATP resolved the tachycardia 955. If not, then high voltage shock therapy can be administered 950.

In some embodiments, the temperature of blood with the coronary sinus can be constantly monitored and old measurements can be retained within the system for a period of time such that old measurements are readily available. For example, in some embodiments the "history" of temperature measurements over the last five minutes is retained in memory. When an arrhythmia is identified based on electrical activity, the system can find a stable temperature within the "history" previous to the onset of the arrhythmia and can calculate the temperature change associated with the arrhythmia as well as the rate of change in temperature, using this information to aid in classifying the event. For example, these steps can be performed as part of operation 930 in FIG. 9.

Figure 10:
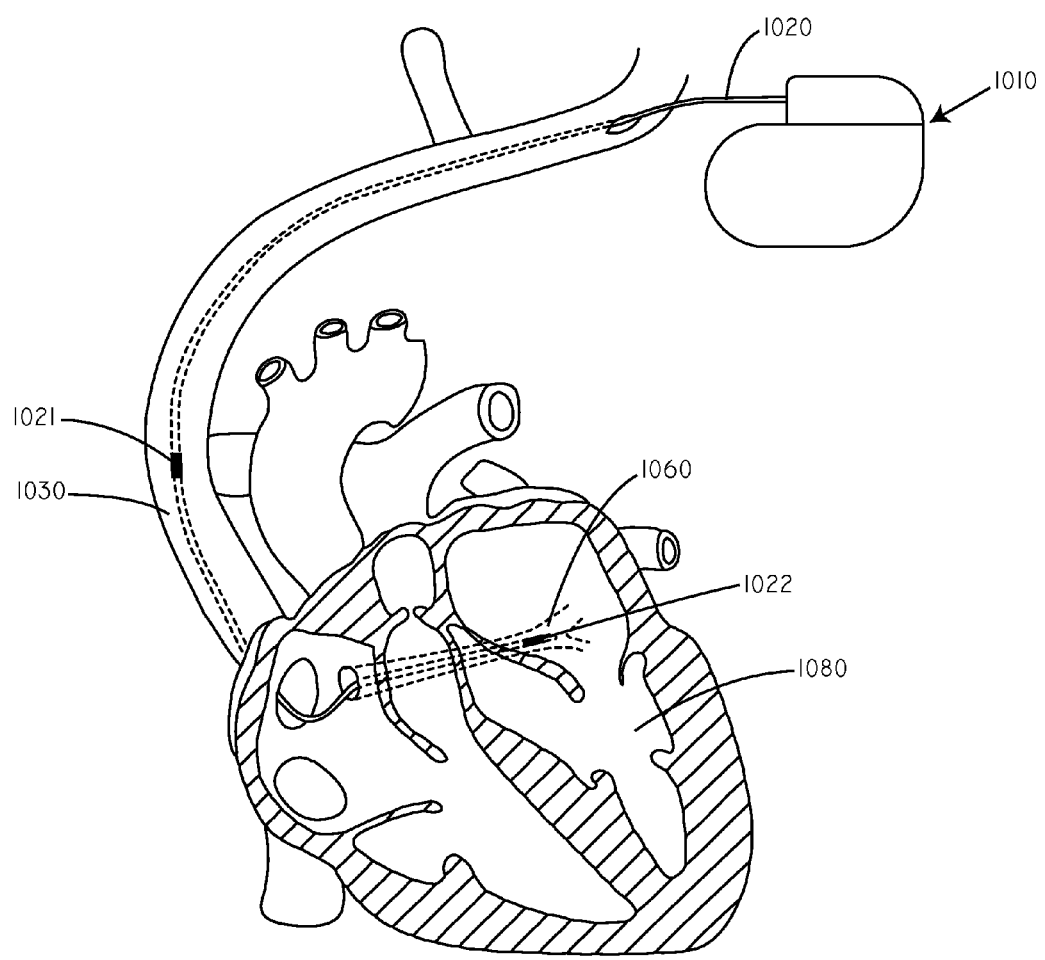
FIG. 10 is a schematic of an additional example implementation consistent with at least one embodiment of the technology disclosed herein.

FIG. 10 is a schematic of an additional example implementation consistent with at least one embodiment of the technology disclosed herein. In this embodiment, a first temperature sensor 1021 is disposed along a lead 1020 substantially within a superior vena cava 1030. The lead 1020 is coupled to a pulse generator or monitor device 1010. A second temperature sensor 1022 is disposed substantially toward the distal end of the lead 1020 substantially within a coronary vein 1060 of a left ventricle 1080. The first temperature sensor 1021, in this embodiment, can be used to control for fluctuations in body core temperature that can affect the second temperature sensor 1022.

Figure 11:
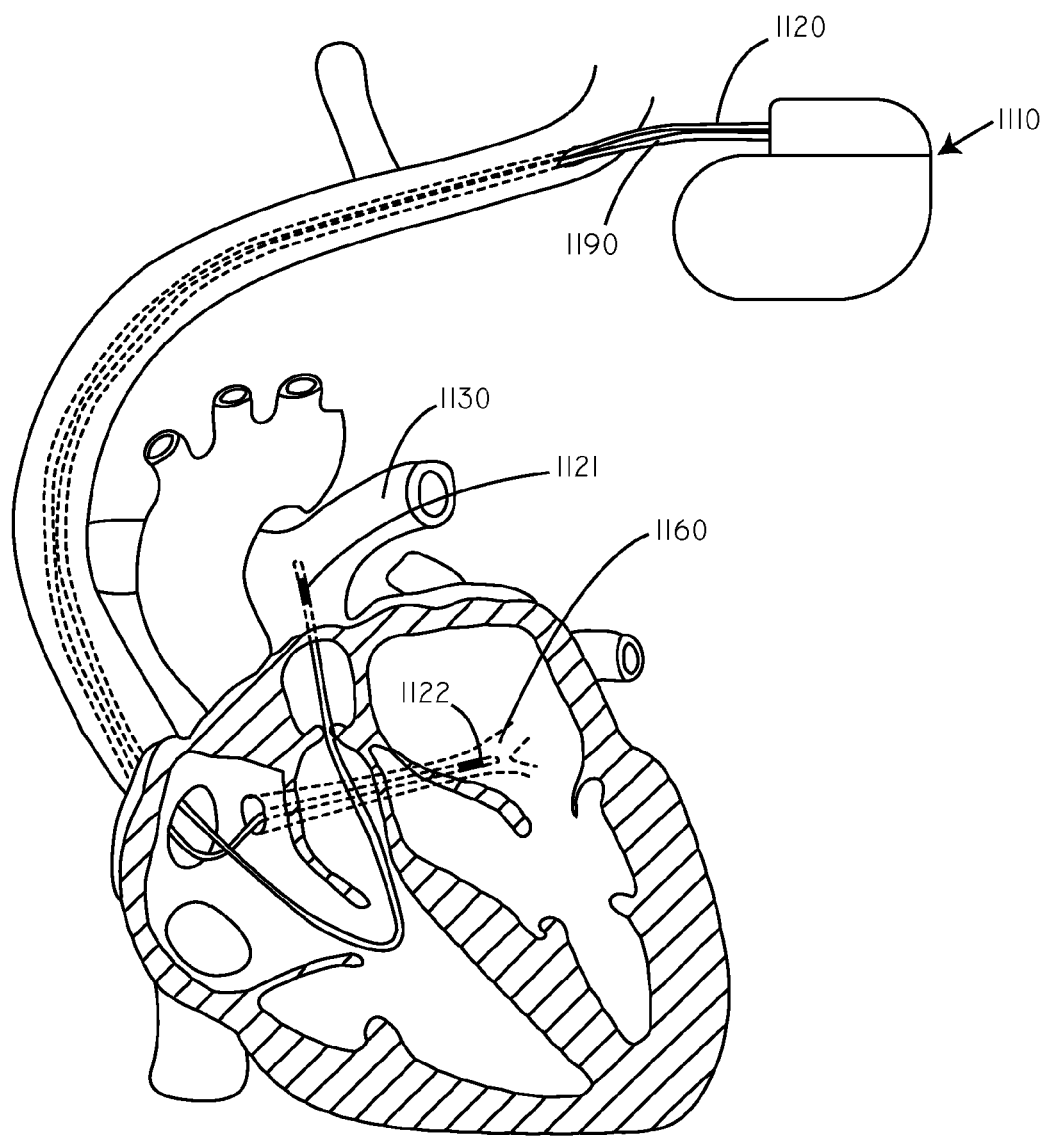
FIG. 11 is a schematic of an additional example implementation consistent with at least one embodiment of the technology disclosed herein.

FIG. 11 is a schematic of an additional example implementation consistent with at least one embodiment of the technology disclosed herein. A first lead 1120 with a first temperature sensor 1122 is coupled to a pulse generator or monitor device 1110. A second lead 1190 with a second temperature sensor 1121 is also coupled to the pulse generator 1110. The first lead 1120 can be positioned so that the first temperature sensor 1122 is within the coronary venous system 1160. The second lead 1190 can be positioned so that the second temperature sensor 1121 is within the pulmonary artery 1130. Temperature measurements from the pulmonary artery 1130 can be used to control for fluctuations in body core temperature that can affect the second temperature sensor 1122 within the coronary venous system 160.

In some embodiments, a second temperature sensor can be disposed on a transeptal lead, passing through the right atrial septum such that the sensor is positioned in the left atrium. In such an embodiment, the lead can be coated with a non-thrombogenic material.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A method of providing treatment to a patient comprising
   monitoring myocardial electrical activity with an electrical sensor;
   identifying the myocardial electrical activity indicative of an arrhythmia;
   charging a capacitor when the arrhythmia is identified;
   measuring the maximum rate of change of blood temperature in the coronary venous system while the capacitor is charging;
   categorizing the arrhythmia as hemodynamically stable, unstable, or severely unstable based on the maximum rate of change of blood temperature in the coronary venous system;
   delivering high-voltage shock therapy by discharging the capacitor if the arrhythmia is categorized as a severely unstable arrhythmia; and
   delivering anti-tachycardia pacing therapy if the arrhythmia is categorized as an unstable arrhythmia.

2. The method of claim 1, further comprising delivering high-voltage shock therapy by discharging the capacitor if the anti-tachycardia pacing does not resolve an identified arrhythmia.

3. The method of claim 1, wherein identifying the myocardial electrical activity indicative of the arrhythmia comprises identifying R-R intervals of less than a previously programmed value.

4. The method of claim 1, further comprising turning on a temperature sensor after the myocardial electrical activity indicative of the arrhythmia is identified.

5. The method of claim 1, further comprising delivering anti-tachycardia pacing therapy if the arrhythmia is categorized as hemodynamically stable.

6. The method of claim 1, wherein identifying the myocardial electrical activity indicative of an arrhythmia comprises identifying R-R intervals of less than a previously programmed value.

7. The method of claim 1, wherein the myocardial electrical activity comprises a time varying electrical potential.

8. The method of claim 1, wherein the high-voltage shock therapy comprises a pulse of current at greater than about 200 volts.

9. The method of claim 1, further comprising using a temperature sensor for said measuring, wherein said temperature sensor is selected from a thermistor, a thermocouple, a fiber optic temperature sensor, and a temperature sensitive diode.

10. The method of claim 1, further comprising measuring temperature in a left atrium to control for fluctuations in body core temperature.

11. The method of claim 1, further comprising measuring temperature in one or more of a left ventricle, a pulmonary artery, and a venous system outside the heart, to control for fluctuations in body core temperature.

12. The method of claim 1, further comprising assessing physical activity with a physical activity sensor to distinguish between sinus tachycardia and other types of tachycardia.

13. An implantable medical system comprising:
    a processor;
    a capacitor;
    an electrical sensor; and
    a temperature sensor;
    the processor configured to monitor myocardial electrical activity with input from the electrical sensor; identify the myocardial electrical activity as indicative of an arrhythmia; charge the capacitor when the arrhythmia is identified; measure a maximum rate of change of temperature of blood in the coronary venous system with input from the temperature sensor while the capacitor is charging; categorize the arrhythmia as hemodynamically stable, unstable, or severely unstable based on the maximum rate of change in the temperature of blood in the coronary venous system; deliver high-voltage shock therapy by discharging the capacitor if the arrhythmia is categorized as to hemodynamically severely unstable; and deliver anti-tachycardia pacing therapy if the arrhythmia is categorized as hemodynamically unstable.

14. The implantable medical system of claim 13, the temperature sensor selected from the group consisting of a thermistor, a thermocouple, a fiber optic temperature sensor, and a temperature sensitive diode.

* * * * *